(12) United States Patent
Mantovani et al.

(10) Patent No.: US 7,915,004 B2
(45) Date of Patent: Mar. 29, 2011

(54) MONOCLONAL ANTIBODIES, HYBRIDOMAS, IMPROVED METHOD FOR DETERMINING THE PROTEIN PTX3 AND KIT FOR SAID DETERMINATION

(75) Inventors: Alberto Mantovani, Milan (IT); Giuseppe Peri, Saronno (IT)

(73) Assignee: Farma Development S.r.l., Rome (IT)

( * ) Notice: Subject to any disclaimer, the term of this patent is extended or adjusted under 35 U.S.C. 154(b) by 718 days.

(21) Appl. No.: 11/587,528

(22) PCT Filed: Apr. 27, 2005

(86) PCT No.: PCT/EP2005/004637
§ 371 (c)(1),
(2), (4) Date: Jan. 9, 2008

(87) PCT Pub. No.: WO2005/106494
PCT Pub. Date: Nov. 10, 2005

(65) Prior Publication Data
US 2008/0261251 A1    Oct. 23, 2008

(30) Foreign Application Priority Data
Apr. 29, 2004   (IT) ............................... MI2004A0858

(51) Int. Cl.
C07K 16/18     (2006.01)
C12N 5/16      (2006.01)
G01N 33/53     (2006.01)
G01N 33/535    (2006.01)
G01N 33/545    (2006.01)
G01N 33/577    (2006.01)
C12P 21/08     (2006.01)

(52) U.S. Cl. ........ 435/7.94; 435/7.1; 435/7.24; 435/7.5; 435/7.92; 435/28; 435/70.21; 435/336; 435/337; 435/343; 436/518; 436/531; 436/548; 436/164; 530/388.24; 530/388.25; 530/388.7; 530/389.3; 530/389.6; 530/391.1

(58) Field of Classification Search .................. 435/7.1, 435/7.24, 7.5, 7.94, 28, 70.21, 336, 337, 435/343, 7.92; 436/518, 531, 548, 164; 530/388.24, 530/388.25, 388.7, 389.3, 389.6, 391.1
See application file for complete search history.

(56) References Cited

U.S. PATENT DOCUMENTS
6,537,745 B2 * 3/2003 Chien et al. .................. 435/5
2004/0137544 A1    7/2004 Latini et al.

OTHER PUBLICATIONS

Boscato et al., 1986. Incidence and specificity of interference in two-site immunoassays. Clinical Chemistry 32: 1491-1495.*
Harlow et al., 1988. Antibodies. A Laboratory Manual, Cold Spring Harbor Laboratory, Cold Spring Harbor. p. 593.*
Hellström et al., 1985. In Monoclonal Antibodies for Cancer Detection and Therapy (Baldwin et al, eds.), Academic Press, London. p. 20.*
Muller et al., 2001. Circulating levels of the long pentraxin PTX3 correlate with severity of infection in critically ill patients. Critical Care Medicine 29: 1404-1407.*
Vouret-Craviari et al., 1997. Expression of a long pentraxin, PTX3, by monocytes exposed to the Mycobacterial cell wall component lipoarabinomannan. Infection and Immunity 65: 1345-1350.*
Fazzini, Fausto et al., "PTX3 in Small-Vessel Vasculitides: An Independent indicator of disease activity produced at sites of inflammation", Arthritis & Rheumatism, vol. 44, No. 12, pp. 2841-2850, 2001.
Breviario, Ferruccio et al., "Cloning of a new gene related to C-reactive protein and serum amyloid P component", The Journal of Biological Chemistry, vol. 267, No. 31, pp. 22190-22197, 1992.
Alles, Victor Vidal et al., "Inducible Expression of PTX3, a New Member of the Pentraxin Family, in Human Mononuclear Phagocytes", Blood, vol. 84, No. 10, pp. 3483-3493, 1994.
Bottazzi, Barbara et al., "Multimer Formation and Ligand Recognition by the Long Pentraxin PTX3—Similarities and differences with the short pentraxins C-reactive protein and serum amyloid P component", The Journal of Biological Chemistry, vol. 272, No. 52, pp. 32817-32823, 1997.
Peri, Giuseppe et al., "PTX3, A Prototypical Long Pentraxin, Is an Early Indicator of Acute Myocardial Infarction in Humans", Circulation, vol. 102, pp. 636-641, 2000.
Latini R. et al., Prognostic significance of the long pentraxin PTX3 in acute myocardial Infarction: comparison with C-reactive protein, NT-proBNP and troponin T. abstract 3091, Supplement IV Circulation , vol. 108, No. 17, p. 680, 2003.

* cited by examiner

*Primary Examiner* — Shafiqul Haq
*Assistant Examiner* — James L Grun
(74) *Attorney, Agent, or Firm* — Oblon, Spivak, McClelland, Maier & Neustadt, L.L.P.

(57) ABSTRACT

Method for determining the level of PTX3 protein in a sample of a biological fluid; hybridoma capable of producing a rat anti-PTX3 monoclonal antibody where said hybridoma is selected from the group comprising MNB10 and Pen-3; specific anti-PTX3 rat monoclonal antibody selected from the monoclonal antibodies produced by the hybridomas MNB10 and Pen-3; kit for determining the level of PTX3 protein in a biological fluid wherein the said kit includes a rat anti-PTX3 monoclonal antibody.

Figure 1:
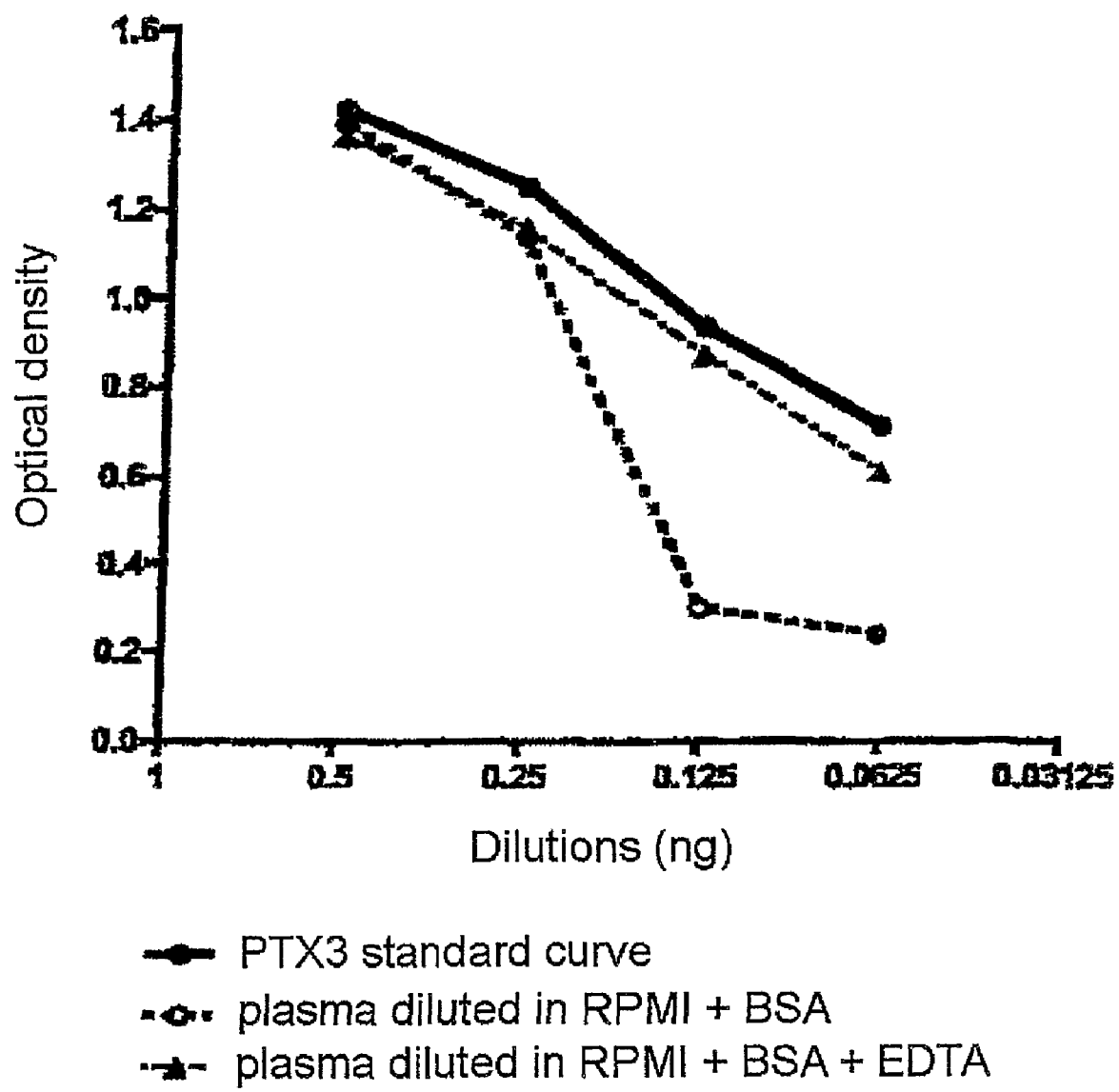

20 Claims, 1 Drawing Sheet

MONOCLONAL ANTIBODIES, HYBRIDOMAS, IMPROVED METHOD FOR DETERMINING THE PROTEIN PTX3 AND KIT FOR SAID DETERMINATION

The present invention relates to rat anti-PTX3 monoclonal antibodies, hybridomas for producing said antibodies, an improved method for determining the protein PTX3 in a biological fluid and a kit for performing said determination.

More particularly, said method, said rat anti-PTX3 monoclonal antibodies and said kit are useful for the early diagnosis of the risk of death in human individuals suffering from cardiovascular and/or cerebrovascular diseases.

The pentraxins, so called on account of their pentameric structure, are a group of proteins which include C-reactive protein (CRP) and serum amyloid P (SAP), produced by the liver in response to inflammatory mediators. The levels thereof in the serum increase in response to various stimuli and have been used for monitoring infections, inflammatory conditions and tissue damage.

PTX3 is a new member of this family which was found in endothelial cells stimulated by interleukin-1 (IL-1). PTX3, a typical long-chain pentraxin, is characterized by a C-terminal region of 203 amino acids which displays homology with the classical pentraxins and by an N-terminal region of 178 amino acids devoid of homology. In contrast to CRP and SAP, PTX3 is produced in various types of cell, principally in endothelial cells and in mononuclear phagocytes, in response to IL-1 and to tumour necrosis factor (TNF), but not to interleukin-6 (IL-6), Further, PTX3 is produced by monocytes in response to components of mycobacterial cell walls and by unstimulated synoviocytes in patients with rheumatoid arthritis.

The protein PTX3 was identified as far back as 1992 (Breviario F. et al. "Cloning of a new gene related to C-reactive protein and serum amyloid P component" *J. Biol. Chem.* 1992, 267: 22190-22197).

It is also known that its production in bacteria was described by Vidal Alles V. et al. in "Inducible expression of PTX3, a new member of the pentraxin family, in human mononuclear phagocytes." *Blood* 1994, 84: 3483-3493, while its production in eukaryotic cells (CHO) has been described by Bottazzi B. et al. "Multimer formation and ligand recognition by the long pentraxin PTX3—Similarities and differences with the short pentraxin C-reactive protein and serum amyloid component." *J. Biol. Chem.* 1997, 272: 32817-32823.

Nonetheless, the biological function of the protein PTX3 has not yet been fully understood.

Recent studies have demonstrated that the levels of PTX3 protein were increased in patients suffering from acute or chronic inflammatory diseases such as sepsis or myocardial infarction. In particular, Peri et al. have reported that the levels of PTX3 protein reach peaks of 6.94±11.26 ng/ml in infarcted patients 7.5 hours after admission to hospital coronary units (*Circulation* 2000, 102: 636-641).

Further, still more recently, it has been observed that the levels of PTX3 protein in infarcted patients are indicative of the risk of death in the three months following the episode (Latini R. et al., "Prognostic significance of the long pentraxin PTX3 in acute myocardial infarction: comparison with C-reactive protein, NT-proBNP and troponin T." abstract 3091, Supplement IV, page 680, *Circulation* 2003, 108 (17),). More particularly, the authors reported that in a representative number of patients with myocardial infarction with elevation of the ST segment the levels of PTX3 protein in the acute phase provide independent information predictive of the risk of death. The same prediction cannot be made on the basis of the levels of C-reactive protein (short chain pentraxin) or of other biocardiac markers such as NT-proBNP or troponin-T.

Further, the inventors are aware of experimental data which show that in patients suffering from cerebral stroke, the level of PTX3 protein is proportional to the damage suffered by the central nervous system.

The determinations of PTX3 reported in the literature [Peri et al., loc. cit.; Muller B. et al., "Circulating levels of the long pentraxin PTX3 correlate with severity of infection in critically ill patients" Crit. Care Med. 2001, 29(7): 1404-1407; Fazzini F. et al., "PTX3 in small-vessel vasculitides—An independent indicator of disease activity produced at sites of inflammation" Arthritis and Rheumatism 2001, 44(12): 2841-2850] were performed by an ELISA method based on a monoclonal antibody specific for PTX3 protein and on a biotinylated polyclonal rabbit IgG specific for PTX3 protein. The aforesaid monoclonal antibody is identified in the literature as MNB4 but the corresponding hybridoma is not accessible to the public.

In particular, the aforesaid method is described in detail by Muller B. et al., loc. cit., and comprises the following steps:

a) 96-well ELISA plates (Nunc Roskilde, Denmark) were coated with 100 µl of rat monoclonal antibody MNB4 (as ascites, diluted 1:5000 in buffer used for the coating) and incubated for one night at 4° C.;

b) the plates were then thoroughly washed with a Dulbecco phosphate buffer saline containing 0.05% Tween 20 (washing buffer) and 200 µl of 5% milk powder to block non-specific binding sites;

c) after incubation for 2 hours at ambient temperature, the plates were again washed 3 times with washing buffer;

d) 50 µl of standard recombinant human PTX3 (from 100 pg/ml to 10 ng/ml) diluted in RPMI 1640 medium (Seromed, Berlin, Germany) and 2% bovine serum albumin (Sigma Chemicals, St. Louis, Mo.) or samples of test plasma, in triplicate, were placed in each well, and the plates were incubated for 2 hours at 37° C.;

e) the plates were washed 3 times with washing buffer and 100 µl of anti-TPX3 rabbit serum, conjugated with biotin, diluted 1:2000 in washing buffer, were added;

f) the plates were incubated for 1 hour at 37° C. and then washed 3 times with 200 µl of washing buffer;

g) 100 µl of streptavidin-peroxidase conjugated with dextran substrate (Amdex, Copenhagen, Denmark), diluted 1:4000, were added to each well, and the plates were incubated for 1 hour at ambient temperature;

h) after the plates had been washed 4 times, 100 µl of the chromogenic substrate ABTS Microwell Peroxidase Substrate System (Kirkegaard and Perry Laboratories, Gaithersburg, Md.) were added;

i) the plates were read at 405 nm with an automatic reader.

One aspect of the present invention is based on the fact that the inventors have observed that the aforesaid known method presents a number of disadvantages.

A first disadvantage of the known method consists in the fact that, in the case of the plasma of some patients, the levels of PTX3 determined at different dilutions of the test plasma sample are not proportional to the dilution performed. The inventors have now found that this disadvantage is surprisingly overcome by adding EDTA to the test plasma sample. In spite of the fact that the reason for this has not yet been entirely elucidated, the inventors postulated, without desiring thereby to limit the scope of the invention, that the observed effect is due to the ability of EDTA to complex $Mg^{++}$ and $Ca^{++}$ ions, so that the same result should also be obtained with other complexing agents.

A second disadvantage consists in the fact that the sensitivity of the known method (ca. 200 pg/ml) is not sufficient for determining PTX3 protein in about 5% of normal subjects. The inventors have now found that the sensitivity of the method can be increased to 75 pg/ml by using novel monoclonal antibodies (step a), changing the concentration of streptavidin-peroxidase (step g) and using a different chromogen (step h).

In one aspect thereof, the invention thus relates to a method for determining the level of PTX3 protein in samples of a biological fluid comprising the following steps:

i) 96-well ELISA plates are coated with 100 µl of a solution containing a rat monoclonal antibody and incubated for one night at 4° C.;

ii) the plates are then washed with a buffer solution and a solution capable of blocking the non-specific binding sites;

iii) after incubation for 2 hours at ambient temperature, the plates are again washed with washing buffer;

iv) in duplicate, 50 µl of standard recombinant human PTX3 diluted in a suitable medium or samples of the biological fluid under test are placed in each well and the plates are incubated for 2 hours at 37° C.;

v) the plates are washed repeatedly with washing buffer and 100 µl of 25 ng/ml biotinylated anti-PTX3 rabbit IgG in washing buffer are then added to each well;

vi) the plates are incubated for 1 hour at 37° C. and then washed repeatedly with washing buffer;

vii) 100 µl of diluted streptavidin-peroxidase are added to each well, and the plates are incubated for 1 hour at ambient temperature;

viii) after the plates have been washed repeatedly with washing buffer, 100 µl of chromogenic substrate are added to each well;

ix) the plates are briefly incubated at ambient temperature, a stop solution is added and the plates are read at 405 nm with an automatic reader;

wherein the improvement consists in the fact that:

the rat monoclonal antibody used in step (i) is the antibody obtained from the hybridoma MNB10 (access No. ABC/PD04001) or from the hybridoma Pen-3 (access No. ABC/PD01004);

the streptavidin-peroxidase used in step (vii) is diluted 1:8000; and the chromogenic substrate used in step (viii) is tetramethylbenzidine (TMB).

Preferably, in step (i) the concentration of rat monoclonal antibody in the solution is about 700 ng/ml. Further, the solution used in step (i) advantageously consists of a coating buffer solution. Preferably the said buffer solution contains 15 mM of carbonate buffer and its pH is 9.6.

Typically, the buffer solution used in step (ii) consists of PBS (phosphate buffer saline)+0.05% of Tween 20. Advantageously, the said solution is used in the amount of about 300 µl/well.

Preferably, the solution capable of blocking non-specific binding sites used in step (ii) consists of a 5% solution of milk powder in a buffer solution consisting of PBS+0.05% of Tween 20. Advantageously, the said solution capable of blocking non-specific binding sites is used in the amount of about 300 µl/well.

The washing specified in step (iii) is preferably repeated 3 times, each time using about 300 µl of solution for each well.

Preferably, in step (iv) the standard recombinant human PTX3 used is placed in the wells in quantities increasing from 75 pg/ml to 1.2 ng. Advantageously, the medium used to dilute the test plasma samples consists of PBS+2% of BSA (bovine serum albumin)+0.18% of $K_3$-EDTA. The presence of EDTA in this solution is very important since, as already stated, the inventors have found that this makes it possible to obtain PTX3 measurements proportional to the dilution performed.

The biotinylated anti-TPX3 rabbit IgG used in step (v) is preferably obtained according Muller B. et al., loc. cit.

Also, the streptavidin-peroxidase used in step (vii) is preferably the horseradish peroxidase-conjugated streptavidin Amdex (RPN 4401 Amersham, Copenhagen, Denmark).

Typically, the stop solution used in step (ix) is a 1M solution of $H_2SO_4$.

Advantageously, the TMB substrate solution used in step (xii) corresponds to the catalogue number 2642 KK of the firm Pharmingen.

In another aspect, the present invention relates to hybridomas capable of producing an anti-PTX3 rat monoclonal antibody and designated MNB 10 and Pen-3. MNB 10 was deposited on Apr. 16, 2004 under the terms of the Budapest Treaty and is identified by Access Number ABC/PD04001 at the Advanced Biotechnology Centre and Pen-3 was deposited on Feb. 8, 2001 under the terms of the Budapest Treaty and is identified as Access Number ABC/PD01004. The full address of the depository is:

Advanced Biotechnology Center (ABC)
Interlab Cell Line Collection
(Biotechnology Dept.)
Largo Rossana Benzi, 10
16132 Genova
Italy.

The selection of the aforesaid hybridomas which produce anti-PTX3 rat monoclonal antibodies according to the invention can be carried out by conventional methods such as those for example described in Example 1 below.

In another aspect, the present invention relates to a specific anti-PTX3 rat monoclonal antibody selected from the group comprising the monoclonal antibodies produced by the aforesaid hybridomas MNB10 and Pen-3.

The preparation of the specific anti-PTX3 rat monoclonal antibodies from the hybridomas of the present invention is not subject to particular restrictions and can be carried out by conventional methods such as those for example described in Example 2 below.

In yet another aspect, the present invention relates to a kit for the determination of the level of PTX3 protein in biological fluids, characterized in that it includes an anti-PTX3 rat monoclonal antibody.

In a preferred embodiment, the determination of the level of PTX3 protein is carried out on the serum of a human individual suffering from a cardiovascular and/or cerebrovascular disease for early diagnosis of their risk of death.

Preferably, the aforesaid kit also includes an anti-PTX3 rabbit polyclonal antibody.

Advantageously, the aforesaid kit also includes purified recombinant PTX3 protein.

In a preferred embodiment, the aforesaid kit also includes streptavidin conjugated with horseradish peroxidase.

Advantageously, the aforesaid kit also includes a washing buffer solution.

Preferably, the aforesaid kit also includes a diluent for the samples of biological fluid to be assayed.

Typically, the aforesaid kit also includes, as chromogen, a solution of tetramethylbenzidine (TMB).

Finally, a stop solution can also be included in the aforesaid kit.

FIG. 1 below and the examples that follow serve further to illustrate the invention, without however limiting it.

FIG. 1 is a diagram which illustrates the effect of EDTA on the plasma of a patient with cardiac decompensation.

In FIG. 1, the dilutions of whole plasma (1:2, 1:4, 1:8 and 1:16) are shown on the x-axis. The optical density is shown on the y-axis.

As can be seen, the levels of PTX3 protein detectable in the serum of a patient with cardiac decompensation in the whole plasma dilution interval between about 1:4 (0.25) and about 1:16 (0.0625) are, in the absence of EDTA, about three times lower than the levels of protein actually present. However, the addition of EDTA makes it possible to obtain levels that essentially correspond to those of the standard curve.

EXAMPLE 1

Hybridoma

Immunisation

Lewis rats are subcutaneously immunised with 200 μg of PTX3 three times at intervals of 15 days. After evaluation of the antibody response by an ELISA assay, the fusion is performed with the animals with the highest antibody titer.

Fusion Protocol

Method a) Preparation of the Splenocytes the spleen of the previously immunised rat is removed under sterile conditions and washed 3 times with 10 ml of DMEM (Dulbecco's modified Eagle's medium), transferred into a plastic Petri dish containing 3 ml of DMEM medium and disaggregated by means of needles and/or crushed with a syringe piston;

the cell suspension is transferred to a test tube, made up to 50 ml with DMEM medium and filtered with a 70 μm screen so as to remove cell aggregates;

wash the splenocytes twice with 50 ml of DMEM medium;

count in Turk.

b) Preparation of the Myeloma "SP2/0"

the myeloma must be in exponential growth phase and not plateau.

wash the cells twice with 50 ml of DMEM medium.

count them c) Fusion add the cells of SP2/0 to the splenocytes so as to obtain a ratio of (5:1) between splenocytes and myeloma;

make up to 50 ml with DMEM and centrifuge at 1700 rpm for 7 min;

draw off the supernatant with a Pasteur pipette taking care to remove it all;

stir the cells that have sedimented, shaking the test tube with the finger and then add 0.6 ml of 37% PEG in DMEM maintained at 37° C.;

with a Pasteur pipette, very slowly resuspend the cells, wait 2 min from when the PEG was added, and then centrifuge at 800 rpm for 6 min;

remove the supernatant with a Pasteur pipette. Resuspend the cells, shaking the test tube gently with the finger and add DMEM maintained at 37° C. drop by drop, up to 20 ml volume;

centrifuge at 1300 rpm for 10 min;

remove the supernatant, and resuspend the pellet of cells very gently with HAT-DMEM using a Pasteur pipette;

dilute them to a concentration of $1.25 \times 10^6 \times ml$ and then seed 0.2 ml of them per well in flat-bottomed 96-well plates, so as to have $2.5 \times 10^5$ cells per well;

incubate the plates at 37° C. in a well humidified incubator and check the presence of colonies after one week;

7 days after the fusion, draw off the medium and add 200 μl of fresh HAT-DMEM;

perform the screening between the $10^{th}$ and $15^{th}$ days after the fusion;

then clone the positive hybridomas in HT-DMEM medium;

after the second cloning, HT-DMEM medium can be replaced with DMEM for hybridomas.

Materials

| DMEM medium | |
|---|---|
| (1x) DMEM | 500 ml |
| L-glutamine | 5 ml |
| gentamicin | 0.5 ml |
| Medium for hybridomas (DMEM) | |
| (1x) DMEM | 500 ml |
| *FCS (fetal calf serum) | 50 ml |
| non-essential AAs (Amino Acids) | 5 ml |
| sodium pyruvate | 5 ml |
| L-glutamine | 5 ml |
| gentamicin | 0.5 ml |
| HAT-DMEM | |
| Myeloma medium + hypoxanthine + aminopterin + thymidine | |
| HT-DMEM | |
| Myeloma medium + hypoxanthine + thymidine | |
| PEG 1550 (polyethylene glycol 1550) 37% | |

Autoclave 7.4 g of PEG (Serva code 33132) in a pyrex bottle. Before it solidifies (ca. 55° C.) add 12.6 ml of DMEM without FCS and mix well. Filter with a 0.2 μm filter, aliquot 1 ml per test tube and store in refrigerator.

EXAMPLE 2

Purification of Monoclonal Antibodies Using Sepharose-Bound Protein G Materials

PBS with Ca and Mg: 450 ml of distilled water+50 ml of PBS (10×)+3 ml of 1M NaOH;

Sepharose Protein G 4 fast flow (Pharmacia cat. 17-0618-01): wash the resin 4 times with PBS by decantation or light centrifugations, then dilute it to 10% with PBS+ 0.1% of sodium azide and store it in the refrigerator;

glycine—0.1M HCl buffer pH 2.8: dissolve 750 mg of glycine in 100 ml of distilled water and adjust to pH 2.8 with 280 μl of 37% HCl;

1.5M TRIS-HCl buffer pH 8.8: dissolve 18.17 g of TRIS in 100 ml of distilled water and adjust to pH 8.8 with 37% HCl;

One 7 ml plastic minicolumn.

Method load the column to 3 ml volume with the resin Sepharose Protein G 4 fast flow;

wash with 20 ml of PBS taking care not to let the resin dry out.

dilute the ascites or the serum 1:3 with PBS, and filter on a 0.2 μm filter;

pass through the resins 4 times and at the end stop the flow at the level of the resin;

wash with 30 ml of PBS;

add 9 ml of pH 2.8 glycine—HCl buffer (3 ml at a time) and collect the eluate in 3 test tubes;

adjust immediately to pH 7 by adding from 100 to 150 μl of pH 8.8 TRIS-HCl buffer;

measure the total proteins and if necessary concentrate them with Centriplus 50 or 100;

dialyse against PBS, aliquot and freeze.

EXAMPLE 3

Method for Determining the Levels of PTX3 in Patients' Plasma 96-well ELISA plates (Nunc MaxiSorp 446612) were coated with 100 µl of a coating buffer solution (15 mM carbonate buffer, pH 9.6) containing purified MNB10 antibody (700 ng/ml) and incubated for one night at 4° C.;

the plates were washed 3 times with 300 µl/well of a washing buffer solution (PBS+0.05% Tween 20) and then 300 µl of washing buffer with 5% of milk powder were added to block non-specific binding sites;

after incubation for 2 hours at ambient temperature, the plates were washed 3 times with washing buffer;

in duplicate, 50 µl of standard recombinant human PTX3 (from 75 pg/ml to 1.2 ng/ml) and samples of the plasma under test diluted in PBS+2% BSA+0.19% $K_3$-EDTA were placed in each well and the plates were incubated for 2 hours at 37° C.

the plates were washed 5 times with washing buffer and 100 µl of 25 ng/ml biotinylated rabbit anti-PTX3 IgG in washing buffer were added to each well;

the plates were incubated for 1 hour at 37° C. and then washed 5 times with 300 µl of washing buffer;

100 µl of horseradish peroxidase-conjugated streptavidin Amdex (RPN 4401 Amersham Copenhagen, Denmark) diluted 1:8000 were added to each well and the plates were incubated for 1 hour at ambient temperature;

after the plates had been washed 5 times with washing buffer, 100 µl of a substrate solution of TMB (tetramethylbenzidine) were added to each well the plates were incubated for 5 minutes at ambient temperature;

50 µl of stop solution ($H_2SO_4$, 1M) were added to each well;

the absorbance at 405 nm was read within 30 minutes from the stopping of the reaction.

EXAMPLE 4

Kit

A kit for determining the levels of PTX3 in human biological fluids comprises:
1. Microplate: 12×8 wells coated with rat anti-PTX3 antibody MNB10.
2. Biotinylated rabbit anti-PTX3 IgG in phosphate buffer solution.
3. Horseradish peroxidase-conjugated streptavidin in phosphate buffer solution.
4. Standards: purified recombinant PTX3 at 2.4, 1, 0.5, 0.2 and 0.05 ng/ml in buffer solution.
5. Washing buffer solution: phosphate buffer saline (PBS) solution.
6. Diluent (to dilute the human biological fluid under test): 1% bovine serum albumin and 0.19% K3-EDTA in phosphate buffer saline solution.
7. Substrate: 0.26 mg/ml tetramethylbenzidine and 0.01% $H_2O_2$ stabilised in 0.05 mol/l citrate buffer (pH 3.8).
8. Stop solution: 1 M $H_2SO_4$.

The invention claimed is:

1. Hybridoma cell line MNB10 identified by Access No. ABC/PD04001 at the Advanced Biotechnology Center of Genoa, Italy.

2. Monoclonal antibody MNB10 produced by the hybridoma cell line MNB10 deposited at the Advanced Biotechnology Center of Genoa, Italy under Access No. ABC/PD04001.

3. A kit comprising the monoclonal antibody MNB10 of claim 2 and a microplate or microtiter plate.

4. A kit comprising the monoclonal antibody MNB10 of claim 2 and one or more ingredients selected from the group consisting of a biotinylated rabbit anti-PTX3 IgG, horseradish peroxidase-conjugated streptavidin, purified long pentraxin PTX3, phosphate buffer solution, washing buffer solution, diluent for a biological sample suspected of containing PTX3, chromogenic substrate, and stop solution.

5. A method for detecting long pentraxin PTX3 in a liquid biological sample comprising:
   contacting a liquid biological sample with the monoclonal antibody MNB10 of claim 2, and
   detecting a presence or an amount of PTX3 in the liquid biological sample based on a presence or an amount of complex formation between said monoclonal antibody and PTX3 in the liquid biological sample.

6. The method of claim 5 which is an Enzyme-Linked Immunosorbent Assay (ELISA) and wherein said monoclonal antibody MNB10 is bound to a microplate or microtiter plate.

7. The method of claim 6, wherein said ELISA comprises a step of binding biotinylated rabbit anti-PTX3 IgG to PTX3 bound to said monoclonal antibody MNB10.

8. The method of claim 7, wherein said ELISA comprises a step of binding streptavidin conjugated with horseradish peroxidase to the biotinylated IgG antibody.

9. The method of claim 8, wherein said ELISA employs tetramethylbenzidine (TMB) as a chromogenic substrate.

10. The method of claim 6, wherein said ELISA comprises:
    binding monoclonal antibody MNB10 to microtiter plate wells, blocking unbound sites and removing unbound material by washing,
    applying the liquid biological sample to which EDTA has been added to said microtiter plate wells under conditions suitable for binding of PTX3 in the sample to the MNB10 monoclonal antibody in said wells, washing to remove unbound material,
    applying a biotinylated anti-PTX3 IgG to said microtiter plate wells under conditions suitable for binding of the IgG to PTX3 bound in said wells, washing to remove unbound material,
    applying streptavidin-peroxidase to said wells under conditions suitable for binding to the biotinylated IgG antibodies bound in said wells, washing to remove unbound material, and
    adding a chromogenic substrate comprising tetramethylbenzidine (TMB).

11. Hybridoma cell line Pen-3 identified by Access No. PD01004 at the Advanced Biotechnology Center of Genoa, Italy.

12. Monoclonal antibody Pen-3 produced by hybridoma cell line Pen-3 identified by Access No. PD01004 at the Advanced Biotechnology Center of Genoa, Italy.

13. A kit comprising the monoclonal antibody Pen-3 of claim 12 and a microplate or microtiter plate.

14. A kit comprising the monoclonal antibody Pen-3 of claim 12 and one or more ingredients selected from the group consisting of a biotinylated rabbit anti-PTX3 IgG, horseradish peroxidase-conjugated streptavidin, purified PTX3, phosphate buffer solution, washing buffer solution, diluent for a biological sample suspected of containing long pentraxin PTX3, chromogenic substrate, and stop solution.

15. A method for detecting long pentraxin PTX3 in a liquid biological sample comprising:
contacting a liquid biological sample with the monoclonal antibody Pen-3 of claim 12, and
detecting a presence or an amount of PTX3 in the liquid biological sample based on a presence or an amount of complex formation between said monoclonal antibody and PTX3 in the liquid biological sample.

16. The method of claim 15 which is an Enzyme-Linked Immunosorbent Assay (ELISA) and wherein said monoclonal antibody is bound to a microplate or microtiter plate.

17. The method of claim 16, wherein said ELISA comprises a step of binding biotinylated rabbit anti-PTX3 IgG to PTX3 bound to said monoclonal antibody Pen-3.

18. The method of claim 17, wherein said ELISA comprises a step of binding streptavidin conjugated with horseradish peroxidase to the biotinylated IgG antibody.

19. The method of claim 18, wherein said ELISA employs tetramethylbenzidine (TMB) as a chromogenic substrate.

20. The method of claim 16, wherein said ELISA comprises:
binding monoclonal antibody Pen-3 to microtiter plate wells, blocking unbound sites and removing unbound material by washing,
applying the liquid biological sample to which EDTA has been added to said microtiter plate wells under conditions suitable for binding of PTX3 in the sample to the PEN-3 monoclonal antibody in said wells, washing to remove unbound material,
applying a biotinylated anti-PTX3 IgG to said microtiter plate wells under conditions suitable for binding of the IgG to PTX3 bound in the wells, washing to remove unbound material,
applying streptavidin-peroxidase to said wells under conditions suitable for binding to the biotinylated IgG antibodies bound in said wells, washing to remove unbound material, and
adding a chromogenic substrate comprising tetramethylbenzidine (TMB).

* * * * *